(12) United States Patent
Mizutani et al.

(10) Patent No.: US 10,041,903 B2
(45) Date of Patent: Aug. 7, 2018

(54) GAS SENSOR ELEMENT AND GAS SENSOR

(71) Applicant: NGK Spark Plug Co., LTD., Nagoya (JP)

(72) Inventors: Masaki Mizutani, Niwa-gun (JP); Nobuo Furuta, Kasugai (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 116 days.

(21) Appl. No.: 15/092,092

(22) Filed: Apr. 6, 2016

(65) Prior Publication Data

US 2016/0305903 A1 Oct. 20, 2016

(30) Foreign Application Priority Data

Apr. 16, 2015 (JP) .................................. 2015-083981

(51) Int. Cl.
*G01N 27/407* (2006.01)

(52) U.S. Cl.
CPC ..... *G01N 27/4071* (2013.01); *G01N 27/4078* (2013.01)

(58) Field of Classification Search
CPC ....................... G01N 27/4078; G01N 27/4071
See application file for complete search history.

(56) References Cited

U.S. PATENT DOCUMENTS

| 4,861,456 A | * | 8/1989 | Mase ................. | G01N 27/4067 204/412 |
|---|---|---|---|---|
| 6,562,215 B1 | * | 5/2003 | Nelson ............... | G01N 27/4071 204/421 |
| 2008/0121020 A1 | * | 5/2008 | Oya ................... | G01N 27/4071 73/31.05 |
| 2013/0233708 A1 | | 9/2013 | Sakuma et al. | |

FOREIGN PATENT DOCUMENTS

JP 2013-185865 A 9/2013

* cited by examiner

*Primary Examiner* — J. Christopher Ball
(74) *Attorney, Agent, or Firm* — Leason Ellis LLP

(57) ABSTRACT

In a cross section of the gas sensor element which is perpendicular to its lengthwise direction and through which all first to fourth lead portions penetrate, when the cross section is bisected into two regions with respect to the width direction of the gas sensor element, the first lead portion and the fourth lead portion are disposed in one of the regions and the second lead portion and the third lead portion are disposed in the other region, and the second lead portion and the third lead portion are disposed so as to be spaced apart from each other in the width direction with no overlap as viewed in a stacking direction.

11 Claims, 6 Drawing Sheets

| DISTANCE X | 0.2 mm | 0.3 mm | 0.4 mm | 0.5 mm | 0.6 mm |
|---|---|---|---|---|---|
| GAP | Generated | Generated | Not generated | Not generated | Not generated |

GAS SENSOR ELEMENT AND GAS SENSOR

This application claims the benefit of Japanese Patent Application No. 2015-083981, filed Apr. 16, 2015, which is incorporated herein by reference in its entity.

FIELD OF THE INVENTION

The present invention relates to a gas sensor element and to a gas sensor.

BACKGROUND OF THE INVENTION

One known gas sensor for detecting the concentration of a particular gas in exhaust gas is a gas sensor element including a cell having a pair of electrodes disposed on outer surfaces of a solid electrolyte body. Particularly, an example of a gas sensor for detecting the concentration of a particular gas in exhaust gas over the entire range is a stacked-type gas sensor element including two cells stacked with a measurement chamber formed therebetween (for example, Japanese Patent Application Laid-Open (kokai) No. 2013-185865). In this stacked-type gas sensor element, in order to adjust a voltage applied to one of the cells to be constant, the other cell pumps oxygen into/from the measurement chamber according to a current inputted from a control circuit. Each cell includes a pair of electrodes, and each electrode includes an electrode portion disposed on a forward end side of the gas sensor element, and a lead portion that electrically connects the electrode portion to an electrode pad disposed on a rear end side of the gas sensor element.

FIG. 7 is a cross-sectional view of the gas sensor element 10 described in Japanese Patent Application Laid-Open (kokai) No. 2013-185865. FIG. 7 shows a cross section of the gas sensor element 10 when it is viewed in a direction from its forward end to its rear end. FIG. 7 shows the arrangement of the lead portions in the cross section of the gas sensor element 10. The gas sensor element 10 includes a first cell 20, an insulating layer 30, a second cell 40, a protection layer 50, and a heater 60. The first cell 20 includes a solid electrolyte body 28 and first and second lead portions 24 and 26 electrically connected to a pair of electrode portions (not shown) disposed on the solid electrolyte body 28. The second cell 40 includes a solid electrolyte body 42 and third and fourth lead portions 44 and 46 electrically connected to a pair of electrode portions (not shown) disposed on the solid electrolyte body 42.

Problems to be Solved by the Invention

Preferably, the lead portions of each pair of electrodes are separated by a large distance from each other in the width direction of the gas sensor element so that the cell can perform accurate sensing and detection. For example, as shown in FIG. 7, in the second cell 40, the fourth lead portion 46 is disposed in a left edge portion of the gas sensor element 10, and the third lead portion 44 is disposed in a central portion of the gas sensor element 10. To sense and detect a more accurate value, it is preferable to increase the widthwise distance between the third lead portion 44 and the fourth lead portion 46. For example, it is preferable to dispose the third lead portion 44 and the fourth lead portion 46 at the left and right edge portions, respectively, of the gas sensor element 10. This applies not only to the second cell 40 but also to the first cell 20.

In the gas sensor element 10, the second lead portion 26 and the third lead portion 44 are generally connected to a common electrode pad. Therefore, in consideration of, for example, formation of through holes for connection to the electrode pad, it is preferable to arrange the second lead portion 26 and the third lead portion 44 such that their widthwise positions are approximately the same as viewed in the direction of stacking.

FIG. 8 is a cross-sectional view of a gas sensor element 10A designed in consideration of the above. As shown in FIG. 8, a second lead portion 26A and a third lead portion 44A are disposed in a left end portion of the gas sensor element 10A, and a first lead portion 24A and a fourth lead portion 46A are disposed in a right end portion of the gas sensor element 10A. This allows the distance between the first lead portion 24A and the second lead portion 26A and the distance between the third lead portion 44A and the fourth lead portion 46A to be increased, so that the gas sensor element 10A can sense and detect a more accurate value. The second lead portion 26A and the third lead portion 44A are disposed so as to overlap as viewed in the stacking direction. This can facilitate, for example, the formation of through holes for connection to the electrode pad for the second lead portion 26A and the third lead portion 44A.

In FIGS. 7 and 8, the second lead portions 26 and 26A overlap the third lead portions 44 and 44A, respectively, as viewed in the stacking direction. Therefore, portions of the gas sensor elements 10 and 10A in which the second lead portions 26 and 26A overlap the third lead portions 44 and 44A, respectively, are thicker than the other portions. In this case, a gap may be generated between the solid electrolyte body 28 and the insulating layer 30 or between the solid electrolyte body 42 and the insulating layer 30 during sintering of the gas sensor element. The generation of the gap may cause a reduction in strength of the gas sensor elements 10 and 10A.

Accordingly, when the first lead portion 24 (24A) to the fourth lead portion 46 (46A) are arranged in the gas sensor element 10 (10A), it is necessary to give consideration to all the issues described above, i.e., suppression of a reduction in the strength of the gas sensor element, ease of formation of the through holes, and improvement in measurement accuracy.

SUMMARY OF THE INVENTION

Means for Solving the Problems

The present invention has been made to solve the foregoing problems and can be embodied in the following modes.

(1) According to one mode of the present invention, a gas sensor element is provided. The gas sensor element has a plate shape extending in a lengthwise direction and comprises a first cell including a first solid electrolyte body and further including a first electrode portion and a second electrode portion that are disposed on opposite principal surfaces, respectively, of the first solid electrolyte body; a second cell including a second solid electrolyte body and further including a third electrode portion and a fourth electrode portion that are disposed on opposite principal surfaces, respectively, of the second solid electrolyte body; a measurement chamber disposed between the first cell and the second cell, the second electrode portion of the first cell and the third electrode portion of the second cell being exposed to the measurement chamber; a first lead portion electrically connected to the first electrode portion and extending from the first electrode portion in the lengthwise direction; a second lead portion electrically connected to the second electrode portion and extending from the second electrode portion in the lengthwise direction; a third lead portion electrically connected to the third electrode portion and extending from the third electrode portion in the lengthwise direction; and a fourth lead portion electrically connected to the fourth electrode portion and extending from the fourth electrode portion in the lengthwise direction, wherein, in a cross section of the gas sensor element which is perpendicular to the lengthwise direction and through which the first to fourth lead portions penetrate, when the cross section is bisected into two regions with respect to a width direction of the gas sensor element, the first lead portion and the fourth lead portion are disposed in one of the regions and the second lead portion and the third lead portion are disposed in the other region, and the second lead portion and the third lead portion are disposed so as to be spaced apart from each other in the width direction with no overlap as viewed in a stacking direction of the gas sensor element. In the gas sensor element of this mode, when the cross section is bisected into two regions with respect to the width direction, the first lead portion is disposed in a region different from the region in which the second lead portion is disposed, and the third lead portion is disposed in a region different from the region in which the fourth lead portion is disposed. Therefore, their widthwise separation distances can be increased, and the cells can perform accurate sensing and detection. In the gas sensor element of this mode, the second lead portion and the third lead portion are disposed in the same region. Therefore, when a single common electrode pad is used for the second lead portion and the third lead portion, through holes for connection to the electrode pad can be easily formed. In the gas sensor element of this mode, in the cross section, the second lead portion and the third lead portion are disposed so as to be spaced apart from each other in the width direction with no overlap as viewed in the stacking direction of the gas sensor element. Therefore, the generation of a gap in the gas sensor element can be suppressed, and a reduction in the strength of the gas sensor element can be suppressed.

(2) In the gas sensor element of the above-described mode, all the first to fourth lead portions may be disposed so as to be separated by at least 0.4 mm from side surfaces of the gas sensor element located on opposite sides thereof with respect to the width direction. In the gas sensor element of this mode, all the first to fourth lead portions are disposed so as to be separated by at least 0.4 mm from the side surfaces of the gas sensor element. Therefore, the generation of fine gaps on the side surfaces of the gas sensor element due to the influence of the thickness of the electrodes can be suppressed, and the strength of the gas sensor element can be well maintained.

(3) In the gas sensor element of the above-described mode, a distance between the second lead portion and the third lead portion in the stacking direction may be shorter than a distance between the first lead portion and the fourth lead portion in the stacking direction. In the gas sensor element of this mode, the distance between the second lead portion and the third lead portion in the stacking direction is short. Therefore, if the second lead portion and the third lead portion are disposed so as to overlap each other as viewed in the stacking direction, the generation of fine gaps in the gas sensor element is significant. However, in the present embodiment, the second lead portion and the third lead portion are disposed so as to be spaced apart from each other in the width direction with no overlaps as viewed in the stacking direction. Therefore, the generation of a gap in the gas sensor element can be suppressed.

(4) The gas sensor element of the above-described mode may further comprise a first insulating layer that has a plate shape, surrounds a circumference of the first solid electrolyte body, and forms part of side surfaces of the gas sensor element located on opposite sides thereof with respect to the width direction, the first lead portion and the second lead portion being disposed on opposite principal surfaces, respectively, of the first insulating layer; and a second insulating layer that has a plate shape, surrounds a circumference of the second solid electrolyte body, and forms part of the side surfaces of the gas sensor element located on the opposite sides thereof with respect to the width direction, the third lead portion and the fourth lead portion being disposed on opposite principal surfaces, respectively, of the second insulating layer. The present mode may be applied to a gas sensor element in which the first and second lead portions are disposed on the first insulating layer surrounding the circumference of the first solid electrolyte body and the third and fourth lead portions are disposed on the second insulating layer surrounding the circumference of the second solid electrolyte body. Also in this case, all the objects described above, i.e., suppression of a reduction in the strength of the gas sensor element, ease of formation of the through holes, and improvement in measurement accuracy, can be achieved.

(5) In the gas sensor element of the above-described mode, the first solid electrolyte body may form part of side surfaces of the gas sensor element located on opposite sides thereof with respect to the width direction, the first lead portion and the second lead portion being disposed on opposite principal surfaces, respectively, of the first solid electrolyte body, and the second solid electrolyte body may form part of the side surfaces of the gas sensor element located on the opposite sides thereof with respect to the width direction, the third lead portion and the fourth lead portion being disposed on opposite principal surfaces, respectively, of the second solid electrolyte body. The present mode may be applied to a gas sensor element in which the first and second lead portions are disposed on the plate-shaped first solid electrolyte body and the third and fourth lead portions are disposed on the plate-shaped second solid electrolyte body. Also in this case, all the objects described above, i.e., suppression of a reduction in the strength of the gas sensor element, ease of formation of the through holes, and improvement in measurement accuracy, can be achieved.

(6) According to another mode of the present invention, a gas sensor is provided. The gas sensor comprises a gas sensor element having a plate shape and extending in a lengthwise direction; a metallic shell having a tubular shape and surrounding a circumference of the gas sensor element; and a packed powder disposed between the gas sensor element and the metallic shell to fix the gas sensor element to the metallic shell, wherein the gas sensor element is the gas sensor element of the above-described mode. In the gas sensor of this mode, when the cross section is bisected with respect to the width direction, the first lead portion is disposed in a region different from the region in which the second lead portion is disposed, and the third lead portion is disposed in a region different from the region in which the fourth lead portion is disposed. Therefore, their widthwise separation distances can be increased, and the cells can perform accurate sensing and detection. In the gas sensor of this mode, the second lead portion and the third lead portion are disposed in the same region. Therefore, when a single common electrode pad is used for the second lead portion and the third lead portion, through holes for connection to the electrode pad can be easily formed. In the gas sensor of this mode, in the cross section, the second lead portion and the third lead portion are disposed so as to be spaced apart from each other in the width direction with no overlap as viewed in the stacking direction of the gas sensor element. Therefore, the generation of a gap in the gas sensor element can be suppressed, and a reduction in the strength of the gas sensor element can be suppressed.

(7) The gas sensor of the above-described mode may be configured such that, in a cross section of a portion of the gas sensor element which contacts the packed powder and is perpendicular to the lengthwise direction, when the cross section is bisected into two regions with respect to the width direction of the gas sensor element, the first lead portion and the fourth lead portion are disposed in one of the regions, and the second lead portion and the third lead portion are disposed in the other region, and the second lead portion and the third lead portion may be disposed so as to be spaced apart from each other in the width direction with no overlap as viewed in the stacking direction. In the gas sensor of this mode, the generation of a gap can be suppressed in a portion of the gas sensor element that is in contact with the packed powder and is required to have particularly high strength. Therefore, in the gas sensor of this mode, a reduction in the strength of the gas sensor element can be suppressed.

The present invention can be implemented in various forms. For example, the present invention can be implemented as a method for producing a gas sensor element.

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF THE INVENTION

Figure 1:
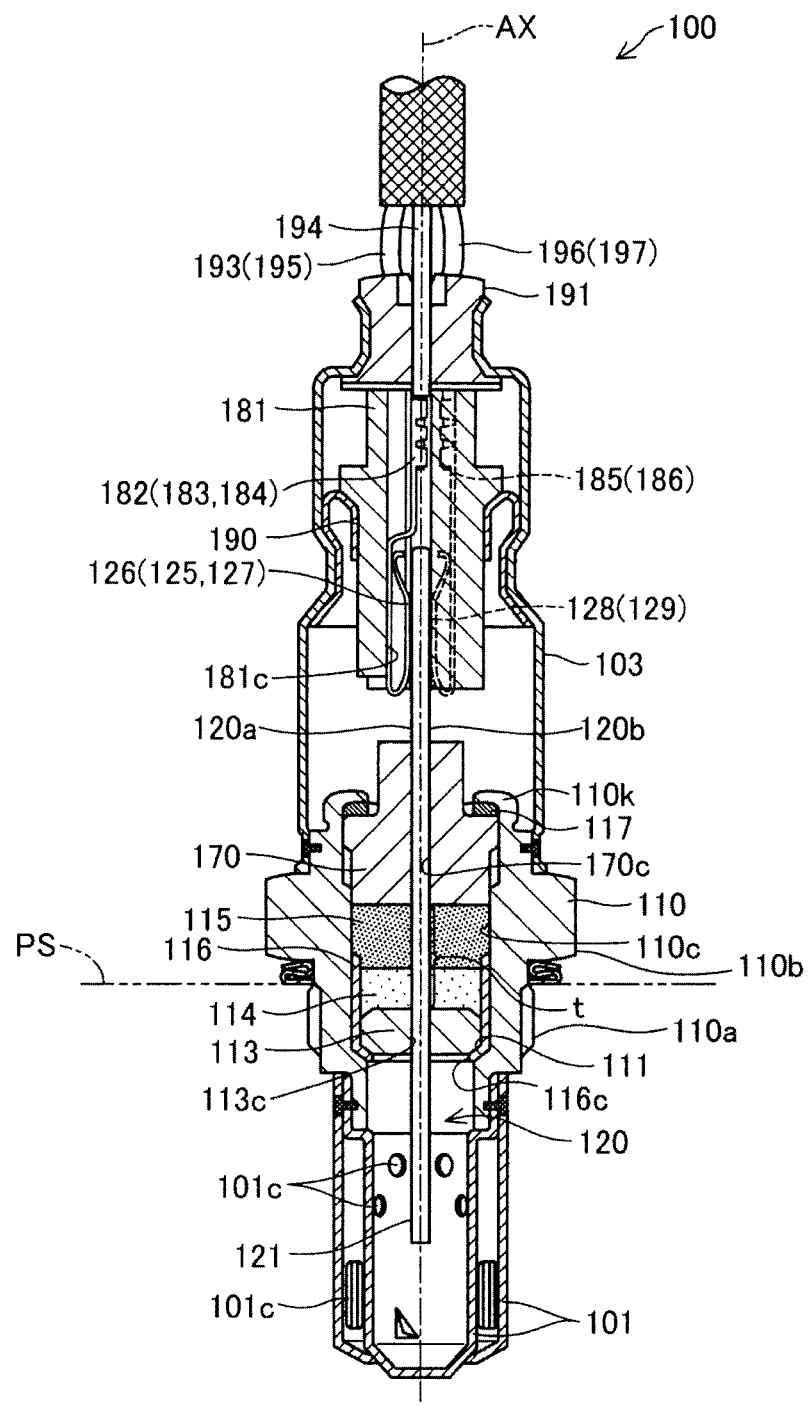
FIG. 1 is a cross-sectional view illustrating the internal structure of a gas sensor 100 according to an embodiment of the present invention.

FIG. 1 is a cross-sectional view illustrating the internal structure of a gas sensor 100 according to an embodiment of the present invention. In FIG. 1, an imaginary center axis AX of the gas sensor 100 (which may be hereinafter referred to simply as an "axial line AX") is shown by a dot-dash line. The gas sensor 100 is a so-called full range air-fuel sensor that is attached to, for example, an exhaust pipe of an internal combustion engine and detects the concentration of a particular gas (for example, oxygen) in exhaust gas, i.e., a gas to be measured, linearly over a range from a rich region to a lean region.

The gas sensor 100 has a shape extending in the direction of the axial line AX. The gas sensor 100 is fixedly attached to the outer surface of the exhaust pipe with a forward end portion (a lower portion in the drawing sheet) of the gas sensor 100 inserted into the exhaust pipe and a rear end portion (an upper portion in the drawing sheet) protruding outward from the exhaust pipe. In FIG. 1, the position of the outer surface of the exhaust pipe with the gas sensor 100 attached thereto is shown by a dash-dot-dot line PS.

The gas sensor 100 includes a metallic shell 110 used to fixedly attach the gas sensor 100 to the exhaust pipe. The metallic shell 110 is a tubular metal member that has a through hole 110c extending in the direction of the axial line AX and surrounds the circumference of a gas sensor element 120. The metallic shell 110 has, on its outer surface, a threaded portion 110a that is to be threadingly engaged with a thread groove formed in the exhaust pipe for attachment of the gas sensor 100, and a tool engagement portion 110b used for engagement with a tool such as a spanner or wrench when the gas sensor 100 is attached to the exhaust pipe.

A closed-bottomed cylindrical double-walled protector 101 is laser-welded to a forward end portion of the metallic shell 110. The double-walled protector 101 has a plurality of introduction holes 101c formed in its inner and outer walls so that exhaust gas can be introduced into the gas sensor 100 after the gas sensor 100 is attached to the exhaust pipe.

A metal-made cylindrical outer tube 103 is laser-welded to a rear end portion of the metallic shell 110. Three sensor lead wires 193, 194, and 195 and two heater lead wires 196 and 197 for electrically connecting the gas sensor 100 to an external control circuit (not shown) are inserted into the gas sensor 100 from the rear end of the outer tube 103. A fluoro rubber-made grommet 191 for sealing the interior of the outer tube 103 is fitted into the rear end of the outer tube 103, and the five lead wires 193 to 197 extend through the grommet 191 and are inserted into the outer tube 103.

The gas sensor 100 includes the gas sensor element 120 that outputs a signal corresponding to the concentration of a particular gas (for example, oxygen). The gas sensor element 120 has a plate-shaped structure extending in a lengthwise direction and has a quadrangular prism shape whose cross section perpendicular to the lengthwise direction is approximately rectangular (details will be described later). As shown in FIG. 1, the lengthwise direction of the gas sensor element 120 is the same as the direction of the axial line AX of the gas sensor 100. The gas sensor element 120 is fixedly held in the through-hole 110c of the metallic shell 110 and is accommodated in the gas sensor 100 along the axial line AX. In FIG. 1, first and second surfaces 120a and 120b of the gas sensor element 120 that face each other in the stacking direction of the gas sensor element 120 face leftward and rightward, respectively, in the drawing sheet.

The gas sensor element 120 has a gas detecting section 121 disposed in its forward end portion (a lower portion in the drawing sheet) and configured to detect the concentration of the particular gas in the exhaust gas. The gas detecting section 121 is accommodated and disposed within the protector 101. Therefore, when the gas sensor 100 is attached to the exhaust pipe, the gas detecting section 121 is exposed to the exhaust gas introduced through the introduction holes 101c.

A separator 181 is fixedly held within the outer tube 103 attached to the rear end portion (an upper portion in the drawing sheet) of the metallic shell 110. The separator 181 is a tubular insulating member having a through hole 181c extending in the direction of the axial line AX. Specifically, the separator 181 is held within the outer tube 103 while being urged toward the grommet 191 by an approximately tubular urging metal member 190 disposed around the separator 181. A rear end portion of the gas sensor element 120 is accommodated within the through-hole 181c of the separator 181.

At the rear end of the gas sensor element 120, three sensor electrode pads 125, 126, and 127 are disposed on the first surface 120a of the gas sensor element 120 and arranged in a direction perpendicular to the drawing sheet so as to be parallel to each other, and two heater electrode pads 128 and 129 are disposed on the second surface 120b and arranged in the direction perpendicular to the drawing sheet so as to be parallel to each other. In addition, three sensor connection terminals 182, 183, and 184 and two heater connection terminals 185 and 186 are disposed within the through-hole 181c of the separator 181 such that these terminals are in contact with the corresponding electrode pads 125 to 129 of the gas sensor element 120. The sensor and heater connection terminals 182 to 186 are electrically connected to the five lead wires 193 to 197, respectively, inserted into the gas sensor 100 through the grommet 191.

A step portion 111 protruding radially inward is formed in a forward end portion of the through hole 110c of the metallic shell 110. A metal cup 116 having a through hole 116c formed in its bottom is disposed within the through-hole 110c of the metallic shell 110 with an outer circumferential edge of the bottom of metal cup 116 engaged with the step portion 111.

A ceramic holder 113 is disposed in an internal space in a bottom portion of the metal cup 116. The ceramic holder 113 is formed of alumina ($Al_2O_3$) and has a rectangular through hole 113c formed at its center for allowing the gas sensor element 120 to pass therethrough.

A first powder layer 114 (talc) is formed within the metal cup 116 in order to airtightly hold the gas sensor element 120 inserted into the through hole 116c of the metal cup 116 and the through hole 113c of the ceramic holder 113. The first powder layer 114 is formed by filling a space above the ceramic holder 113 with talc powder. The gas sensor element 120 is thereby integrated with the metal cup 116, the ceramic holder 113, and the first powder layer 114 and is held in the through hole 110c of the metallic shell 110.

In addition, a second powder layer 115 (talc) made of packed talc powder is formed on the first powder layer 114 within the through hole 110c of the metallic shell 110 in order to ensure airtightness between a rear end portion of the metallic shell 110 and the gas detecting section 121 of the gas sensor element 120. A ceramic sleeve 170 is disposed on the second powder layer 115. The packed powder forming the second powder layer 115 fixes the gas sensor element 120 to the metallic shell 110.

The ceramic sleeve 170 is a tubular member having a rectangular axial hole 170c extending in the direction of the axial line AX for allowing the gas sensor element 120 to pass therethrough. The ceramic sleeve 170 may be formed of alumina. A rear end portion 110k of the metallic shell 110 is crimped; i.e., bent radially inward, whereby the ceramic sleeve 170 is pressed toward the second powder layer 115 and fixed to the metallic shell 110. A crimp ring 117 is disposed between the ceramic sleeve 170 and the rear end portion 110k of the metallic shell 110.

Figure 2:
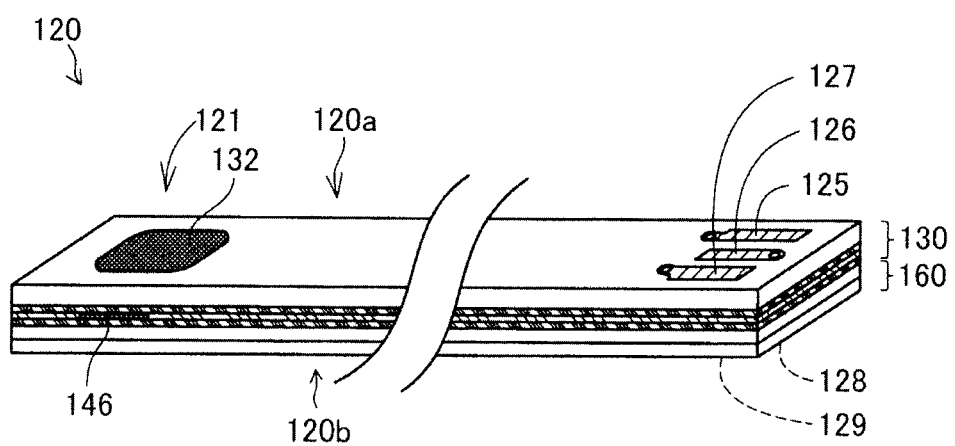
FIG. 2 is a schematic perspective view illustrating the structure of a gas sensor element 120.

FIG. 2 is a schematic perspective view illustrating the structure of the gas sensor element 120. In FIG. 2, the gas sensor element 120 is illustrated with the first surface 120a facing upward and the second surface 120b facing downward. The direction of the axial line AX (FIG. 1) corresponds to the horizontal direction in the drawing sheet. The forward end side of the gas sensor element 120 corresponds to the left side in the drawing sheet, and the rear end side corresponds to the right side. The gas sensor element 120 is produced by stacking a plate-shaped detecting element 130 (on the upper side in the drawing sheet) on a plate-shaped heater 160 (on the lower side in the drawing sheet) and then integrating them by firing.

As described earlier with reference to FIG. 1, the gas detecting section 121 is formed in the forward end portion of the gas sensor element 120. In addition, the three electrode pads 125 to 127 are arranged on the first surface 120a to be located on the rear end side of the gas sensor element 120. Although not illustrated, the two electrode pads 128 and 129 are arranged on the second surface 120b to be located on the rear end side of the gas sensor element 120.

Figure 3:
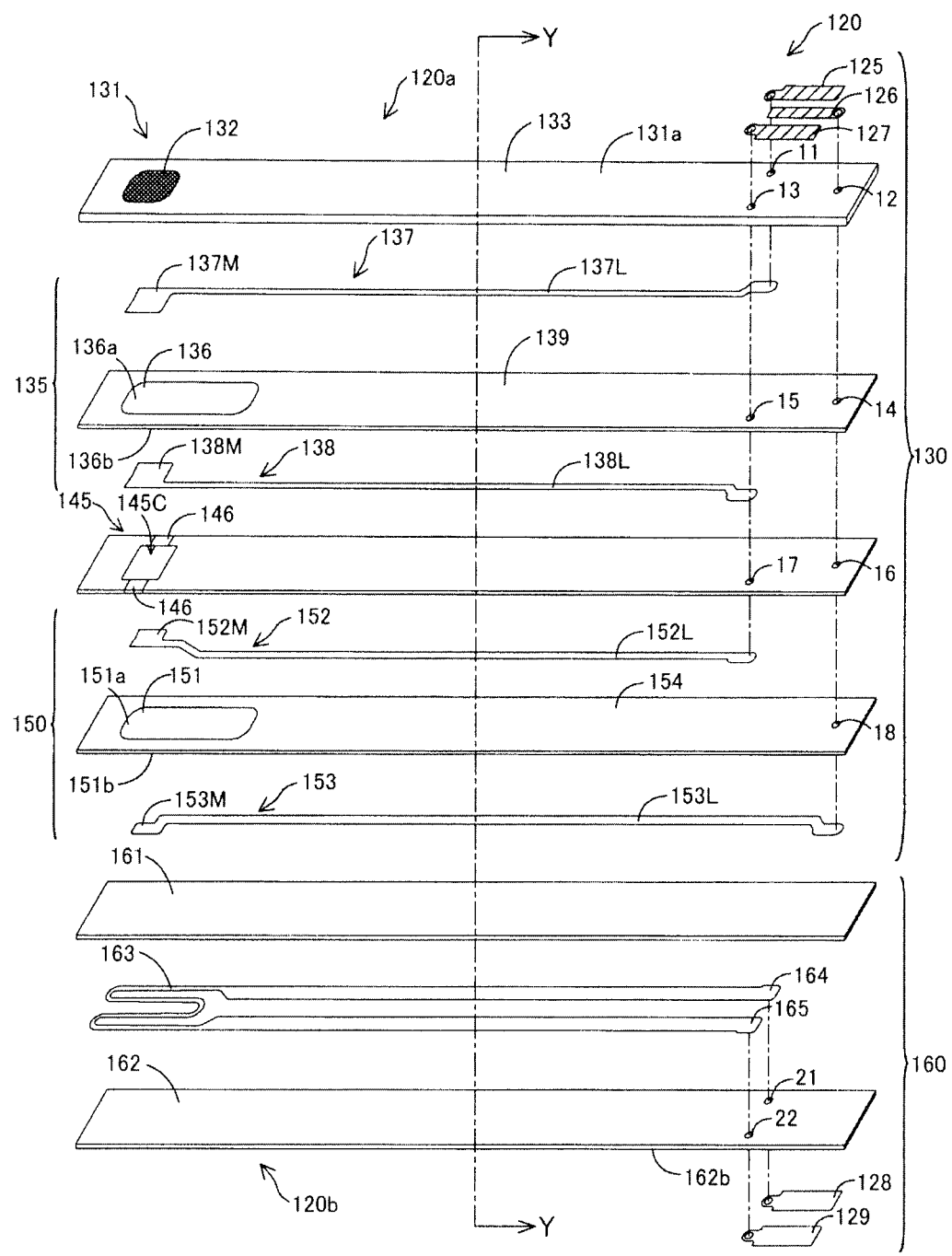
FIG. 3 is an exploded perspective view of the gas sensor element 120.

FIG. 3 is an exploded perspective view of the gas sensor element 120. In FIG. 3, the components of the gas sensor element 120 shown are disassembled in the stacking direction (the vertical direction in the drawing sheet). The left side in the drawing sheet corresponds to the forward end side of the gas sensor element 120, and the right side corresponds to the rear end side. In FIG. 3, dot-dash lines indicate that components connected by the dot-dash lines electrically communicate with each other. The detecting element 130 of the gas sensor 100 includes a protection layer 131, an oxygen pump cell 135 serving as a first cell, an insulating layer 145, and an oxygen concentration detection cell 150 serving as a second cell that are stacked in this order from the first surface 120a side.

The protection layer 131 is a plate-shaped member formed mainly of alumina and protects a surface of the gas sensor element 120 on the first surface 120a side. The protection layer 131 has a porous section 132 that is formed in its forward end portion and is gas-permeable in the stacking direction (in the vertical direction in the drawing sheet), and a base section 133 is disposed so as to surround the circumference of the porous section 132. The porous section 132 is formed is a region that overlaps a first electrode portion 137M described later when the gas sensor element 120 is viewed in the stacking direction. The porous section 132 functions as a gas flow channel for pumping the exhaust gas into/from the gas detecting section 121.

The three electrode pads 125 to 127 are disposed in a rear end portion of an outer surface 131a of the base section 133 of the protection layer 131 and arranged in the width direction of the gas sensor element 120 (in the direction perpendicular to the drawing sheet) so as to be parallel to each other. First to third through-hole conductors 11 to 13 for the first to third electrode pads 125 to 127 are formed in the base section 133 so as to extend through the base section 133.

The oxygen pump cell 135 includes a plate-shaped first solid electrolyte body 136, a first insulating layer 139 that surrounds the circumference of the first solid electrolyte body 136, and electrodes (a first electrode 137 and a second electrode 138) disposed on opposite principal surfaces, respectively, of the first solid electrolyte body 136 and the first insulating layer 139. The solid electrolyte body 136 is a plate-shaped member formed mainly of zirconia ($ZrO_2$) and having an area slightly larger than the area of a first electrode portion 137M and the area of a second electrode portion 138M. The first insulating layer 139 is a plate-shaped member formed mainly of alumina. The first insulating layer 139 surrounds and covers the outer circumference of the first solid electrolyte body 136, has approximately the same size as the size of the protection layer 131, and forms part of side surfaces of the gas sensor element 120. Fourth and fifth through-hole conductors 14 and 15 that electrically communicate with the second and third through-hole conductors 12 and 13 formed in the protection layer 131 are formed in a rear end portion of the first insulating layer 139 so as to extend through the first insulating layer 139.

The first electrode 137 and the second electrode 138 are porous bodies formed mainly of platinum (Pt). The first electrode 137 has the first electrode portion 137M and a first lead portion 137L electrically connected with the first electrode portion 137M and extending from the first electrode portion 137M in the lengthwise direction. The second electrode 138 has the second electrode portion 138M and a second lead portion 138L electrically connected with the second electrode portion 138M and extending from the second electrode portion 138M in the lengthwise direction.

The first electrode portion 137M is disposed on a first surface 136a of the first solid electrolyte body 136 (the upper surface in the drawing sheet), and the second electrode portion 138M is disposed on a second surface 136b of the first solid electrolyte body 136 (the lower surface in the drawing sheet). When the gas sensor 100 is attached to the exhaust pipe, the first electrode portion 137M disposed on the first surface 136a is exposed to the exhaust gas through the porous section 132 disposed in the protection layer 131.

The first lead portion 137L of the first electrode 137 is disposed on the first insulating layer 139 and electrically communicates with the first electrode pad 125 through the first through-hole conductor 11 in the protection layer 131. The second lead portion 138L of the second electrode 138 is disposed on the first insulating layer 139 and electrically communicates with the third electrode pad 127 through the fifth through-hole conductor 15 formed in the first insulating layer 139 and the third through-hole conductor 13 formed in the protection layer 131.

The insulating layer 145 is a plate-shaped insulating member formed mainly of alumina and having approximately the same size as the size of the first insulating layer 139 of the oxygen pump cell 135. The insulating layer 145 is stacked between the oxygen pump cell 135 and the oxygen concentration detection cell 150 to insulate the oxygen pump cell 135 and the oxygen concentration detection cell 150 from each other. An opening is formed in a forward end portion of the insulating layer 145. The opening forms a measurement chamber 145c when the insulating layer 145 is sandwiched between the oxygen pump cell 135 and the oxygen concentration detection cell 150. The exhaust gas (measurement gas) is introduced into the measurement chamber 145c. The measurement chamber 145c is disposed between the oxygen pump cell 135 and the oxygen concentration detection cell 150, and the second electrode portion 138M of the oxygen pump cell 135 and a third electrode portion 152M (described later) of the oxygen concentration detection cell 150 are exposed to the measurement chamber 145c.

Diffusion controlling portions 146 are formed in two side wall portions of the insulating layer 145 which face each other in the width direction of the insulating layer 145 with the opening intervening therebetween. The diffusion controlling portions 146 are formed of gas-permeable porous alumina. In the gas sensor element 120, the exhaust gas is introduced into the measurement chamber 145c in an amount corresponding to the gas permeability of the diffusion controlling portions 146. Specifically, the diffusion controlling portions 146 function as gas introduction portions of the gas detecting section 121.

A seventh through-hole conductor 17 that electrically communicates with the second lead portion 138L of the second electrode 138 of the oxygen pump cell 135 is formed in a rear end portion of the insulating layer 145 so as to extend through the insulating layer 145. A sixth through-hole conductor 16 that electrically communicates with the fourth through-hole conductor 14 formed in the first insulating layer 139 of the oxygen pump cell 135 is formed in a position adjacent to the seventh through-hole conductor 17 so as to extend through the insulating layer 145.

The oxygen concentration detection cell 150 includes a plate-shaped second solid electrolyte body 151, a second insulating layer 154 that surrounds the circumference of the second solid electrolyte body 151, and electrodes (a third electrode 152 and a fourth electrode 153) disposed on opposite principal surfaces, respectively, of the second solid electrolyte body 151 and the second insulating layer 154. The second solid electrolyte body 151 is a plate-shaped member formed mainly of zirconia and having an area slightly larger than the areas of a pair of electrode portions (a third electrode portion 152M and a fourth electrode portion 153M). The second insulating layer 154 is a plate-shaped member formed mainly of alumina. The second insulating layer 154 surrounds and covers the outer circumference of the second solid electrolyte body 151, has approximately the same size as the size of the insulating layer 145, and forms part of the side surfaces of the gas sensor element 120. An eighth through-hole conductor 18 is formed in a rear end portion of the second insulating layer 154 so as to extend through the second insulating layer 154. The eighth through-hole conductor 18 electrically communicates with the sixth through-hole conductor 16 formed in the insulating layer 145.

The third electrode 152 and the fourth electrode 153 are porous bodies formed mainly of platinum (Pt). The third electrode 152 has the third electrode portion 152M and a third lead portion 152L electrically connected to the third electrode portion 152M and extending from the third electrode portion 152M in the lengthwise direction. The fourth electrode 153 has the fourth electrode portion 153M and a fourth lead portion 153L electrically connected to the fourth electrode portion 153M and extending from the fourth electrode portion 153M in the lengthwise direction. The third electrode portion 152M is disposed on a first surface 151a of the second solid electrolyte body 151 (the upper surface in the drawing sheet), and the fourth electrode portion 153M is disposed on a second surface 151b of the second solid electrolyte body 151 (the lower surface in the drawing sheet). The third electrode portion 152M disposed on the first surface 151a is exposed to the measurement chamber 145c.

The third lead portion 152L of the third electrode 152 is disposed on the second insulating layer 154 and electrically communicates with the second electrode 138 of the oxygen pump cell 135 and the third electrode pad 127 through the seventh through-hole conductor 17 formed in the insulating layer 145. The fourth lead portion 153L of the fourth electrode 153 is disposed on the second insulating layer 154 and electrically communicates with the second electrode pad 126 through the eighth through-hole conductor 18 formed in the second insulating layer 154, the fourth through-hole conductor 14 formed in the insulating layer 145, and the second through-hole conductor 12 formed in the protection layer 131. Specifically, the third electrode 152 and the second electrode 138 have the same potential.

The heater 160 includes first and second insulators 161 and 162, a heat-generating resistor 163, and first and second heater lead portions 164 and 165. Each of the first and second insulators 161 and 162 is a plate-shaped member formed of alumina and having the same size as the detecting element 130. The first and second insulators 161 and 162 hold the heat-generating resistor 163 and the heater lead portions 164 and 165 therebetween.

The heat-generating resistor 163 is a heating element formed from a heat-generating wire made mainly of platinum and having a meandering shape. The two heater lead portions 164 and 165 are connected to opposite ends of the heat-generating resistor 163 and extend rearward from the heat-generating resistor 163.

First and second heater electrode pads 128 and 129 are disposed in a rear end portion of an outer surface 162b of the second insulator 162 and arranged in the width direction of the heater 160 so as to be parallel to each other. First and second heater through-hole conductors 21 and 22 for the first and second heater electrode pads 128 and 129 are formed in the second insulator 162 so as to extend through the second insulator 162. The first and second heater lead portions 164 and 165 connected to the heat-generating resistor 163 electrically communicate with the first and second heater electrode pads 128 and 129, respectively, through the first and second heater through-hole conductors 21 and 22.

During operation of the gas sensor 100, the heating temperature of the heater 160 is controlled by an external heater control circuit (not shown). The heater 160 heats the detecting element 130 to several hundred degrees C. (for example, 700 to 800° C.) to activate the oxygen pump cell 135 and the oxygen concentration detection cell 150.

Figures 4, 5:
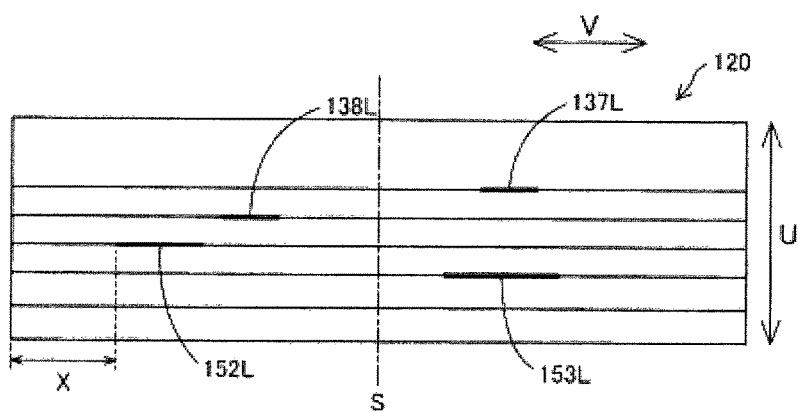
FIG. 4 is a cross-sectional view of the gas sensor element 120 taken along line Y-Y in FIG. 3.
FIG. 5 is a table showing the distance X between a lead portion and a side surface and the generation of a gap on the side surface.

FIG. 4 is a cross-sectional view of the gas sensor element taken along line Y-Y in FIG. 3. The Y-Y cross section is a cross section which is perpendicular to the lengthwise direction of the gas sensor element 120 and through which all the first to fourth lead portions 137L to 153L (i.e., the first lead portion 137L, the second lead portion 138L, the third lead portion 152L, and the fourth lead portion 153L) pass.

In the Y-Y cross section, when the Y-Y cross section is bisected into two regions with respect to the width direction V of the gas sensor element 120 that is perpendicular to the stacking direction U of the oxygen pump cell 135 and the oxygen concentration detection cell 150, the first lead portion 137L and the fourth lead portion 153L are disposed in one of the regions and the second lead portion 138L and the third lead portion 152L are disposed in the other region. For ease of comprehension, a line that bisects the gas sensor element 120 with respect to the width direction V is illustrated as a dot-dash line S in FIG. 4. Specifically, the region in which the first lead portion 137L and the fourth lead portion 153L are disposed is a right-side region (on the right side in the drawing sheet) with respect to the dot-dash line S, and the region in which the second lead portion 138L and the third lead portion 152L are disposed is a left-side region (on the left side in the drawing sheet) with respect to the dot-dash line S.

Since the first to fourth lead portions 137L to 153L are disposed in the manner described above, the widthwise distance between the first lead portion 137L and the second lead portion 138L and the widthwise distance between the third lead portion 152L and the fourth lead portion 153L can be increased, so that the cells can perform accurate sensing and detection. From the viewpoint of improvement in measurement accuracy, the widthwise distance between the first lead portion 137L and the second lead portion 138L and the widthwise distance between the third lead portion 152L and the fourth lead portion 153L are preferably equal to or longer than one-third of the width of the gas sensor element 120 and more preferably equal to or longer than one-half of the width. The distance between the first lead portion 137L and the second lead portion 138L is the distance from an end point of the first lead portion 137L that is closer to the second lead portion 138L to an end point of the second lead portion 138L that is closer to the first lead portion 137L. The distance between the third lead portion 152L and the fourth lead portion 153L is the distance from an end point of the third lead portion 152L that is closer to the fourth lead portion 153L to an end point of the fourth lead portion 153L that is closer to the third lead portion 152L.

Generally, the second lead portion 138L and the third lead portion 152L are connected to a common electrode pad, i.e., the third electrode pad 127. Therefore, in consideration of the formation of the through-hole conductors connected to the third electrode pad 127 (the third through-hole conductor 13, the fifth through-hole conductor 15, and the seventh through-hole conductor 17) and the formation of the through holes for these through-hole conductors, it is preferable to dispose the second lead portion 138L and the third lead portion 152L at approximately the same widthwise position as viewed in the stacking direction.

In the present embodiment, the distance between the second lead portion 138L and the third lead portion 152L in the stacking direction is shorter than the distance between the first lead portion 137L and the fourth lead portion 153L in the stacking direction. Therefore, if the second lead portion 138L and the third lead portion 152L are disposed so as to overlap each other as viewed in the stacking direction, the overlapping portion in which the second lead portion 138L overlaps the third lead portion 152L is thicker than the other portion. In this case, gaps may be generated between the first insulating layer 139 and the insulating layer 145 and between the insulating layer 145 and the second insulating layer 154 during, for example, firing of the gas sensor element. The generation of gaps may cause a reduction in the strength of the sensor element 120. However, in the gas sensor element 120 of the present embodiment, the second lead portion 138L and the third lead portion 152L are disposed so as to be spaced apart from each other in the width direction V with no overlap as viewed in the stacking direction U. This can suppress the generation of gaps in the gas sensor element 120. In addition, a reduction in the strength of the gas sensor element 120 caused by the generation of gaps can be suppressed.

The Y-Y cross section is a cross section of a portion of the gas sensor element 120, which portion is in contact with the packed powders within the gas sensor 100. In other words, the Y-Y cross section is a cross section of a portion t (see FIG. 1) of the gas sensor element 120, which portion is in contact with the packed powder layers (the first powder layer 114 and the second powder layer 115). In the portion t, the pressure applied to the gas sensor element 120 is higher than in the other portions. Therefore, by suppressing the generation of gaps in the portion t of the gas sensor element, which is required to have particularly high strength, the strength of this portion can be improved. The gas sensor element 120 may be such that the above requirement is met in a cross section of a portion other than the portion of the gas sensor element 120 which is in contact with the packed powders.

All the lead portions, i.e., the first lead portion 137L to the fourth lead portion 153L, are disposed such that they are separated by at least 0.4 mm from the side surfaces of the gas sensor element 120. In the gas sensor element 120, the third lead portion 152L is closest to the side surfaces. The distance X between the third lead portion 152L and one of the side surface is 0.4 mm or longer. In this manner, the generation of fine gaps on the side surfaces of the gas sensor element 120 due to the influence of the thickness of the electrodes can be further suppressed.

FIG. 5 is a table showing the distance X between a lead portion and a side surface and the generation of a small gap in the side surface. The presence or absence of a fine gap was checked by a liquid penetrant test. Specifically, a red test solution was applied to the side surfaces of a gas sensor element 120. When the red test solution permeated a side wall, it was judged that a fine gap was present. When the red test solution did not permeate the side walls, it was judged that no fine gap was present. The gas sensor elements used were produced in the same manner as the method of producing the gas sensor element in the above embodiment except that the distance X was made different among the gas sensor elements. As can be seen from the results in FIG. 4, it was found that, although fine gaps generated when the distance X was less than 0.4 mm, no fine gaps generated when the distance X was 0.4 mm or more.

The present invention is not limited to the above described embodiments, examples, and modifications and may be embodied in various other forms without departing from the spirit of the invention. For example, the technical features in the embodiments, examples, and modifications corresponding to the technical features in the modes described in Summary of the Invention can be appropriately replaced or combined to solve some of or all the foregoing problems or to achieve some of or all the foregoing effects. A technical feature which is not described as an essential feature in the present specification may be appropriately deleted.

In the gas sensor element 120 of the present embodiment, electrodes (the first electrode 137 and the second electrode 138) are disposed on opposite principal surfaces, respectively, of the first solid electrolyte body 136 and the first insulating layer 139, and electrodes (the third electrode 152 and the fourth electrode 153) are disposed on opposite principal surfaces, respectively, of the second solid electrolyte body 151 and the second insulating layer 154. However, a gas sensor element 120A shown in FIG. 6 may be used. This gas sensor element 120A is the same as the gas sensor element 120 except that the structure of the first solid electrolyte body 136 and the first insulating layer 139 and the structure of the second solid electrolyte body 151 and the second insulating layer 154 in the gas sensor element 120A are different from those of the gas sensor element 120. Description of the same portions will be omitted.

Figure 6:
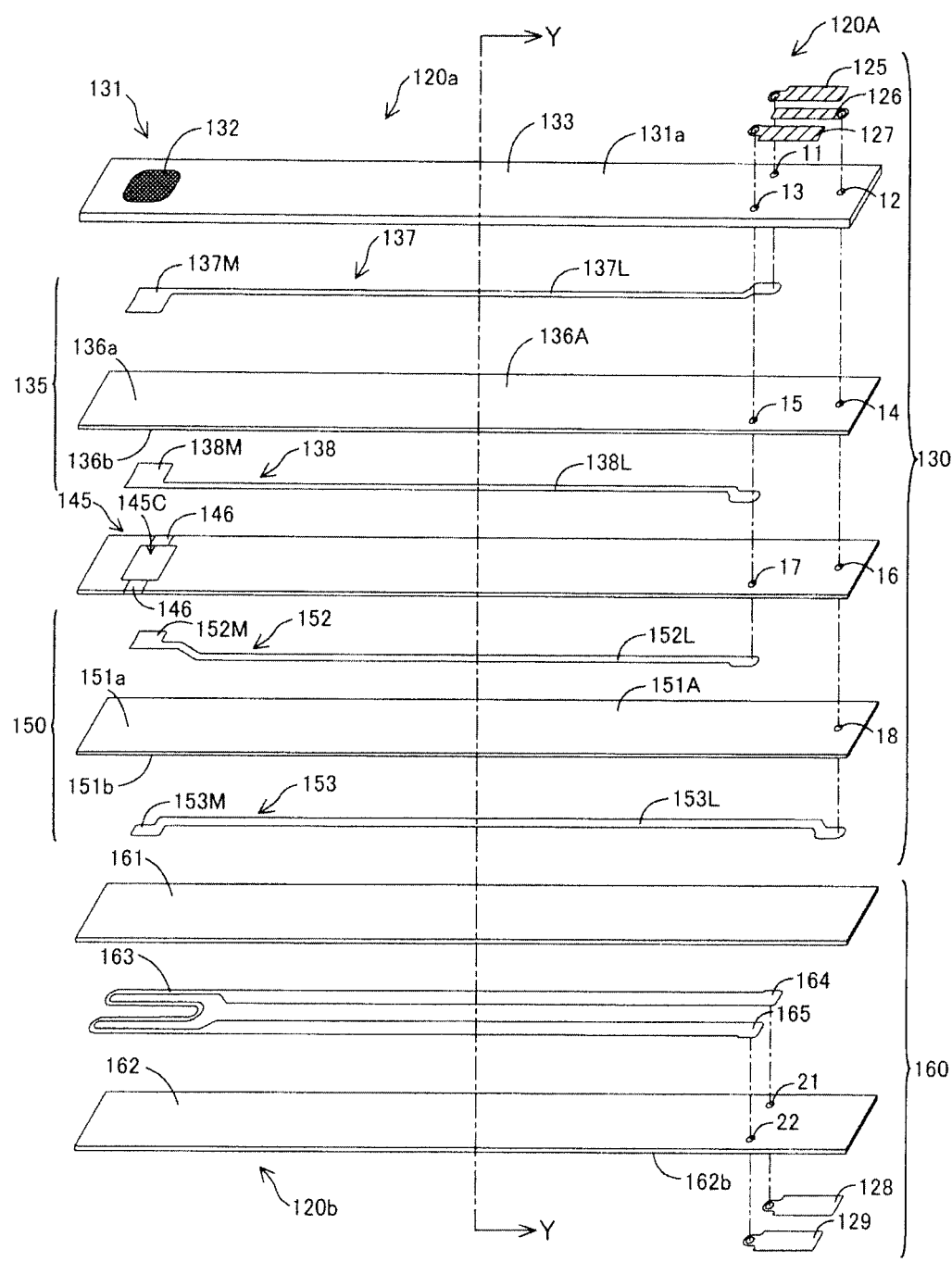
FIG. 6 is an exploded perspective view of a gas sensor element 120A.
Figure 7:
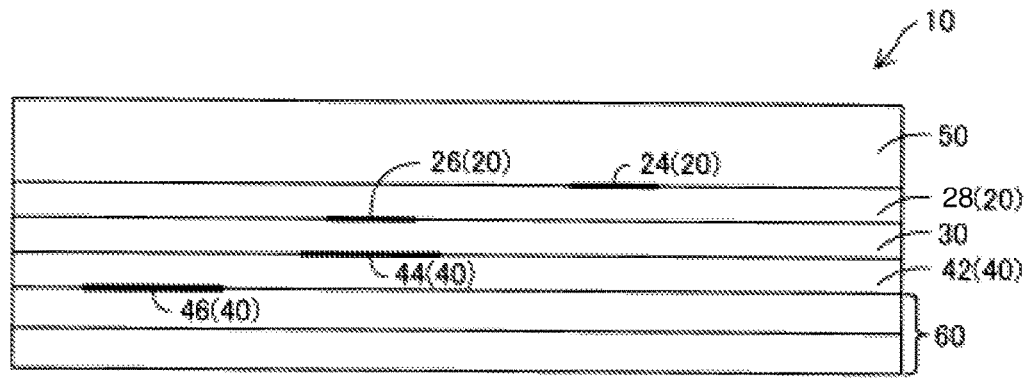
FIG. 7 is a cross-sectional view of a gas sensor element 10 described in Japanese Patent Application Laid-Open (kokai) No. 2013-185865.
Figure 8:
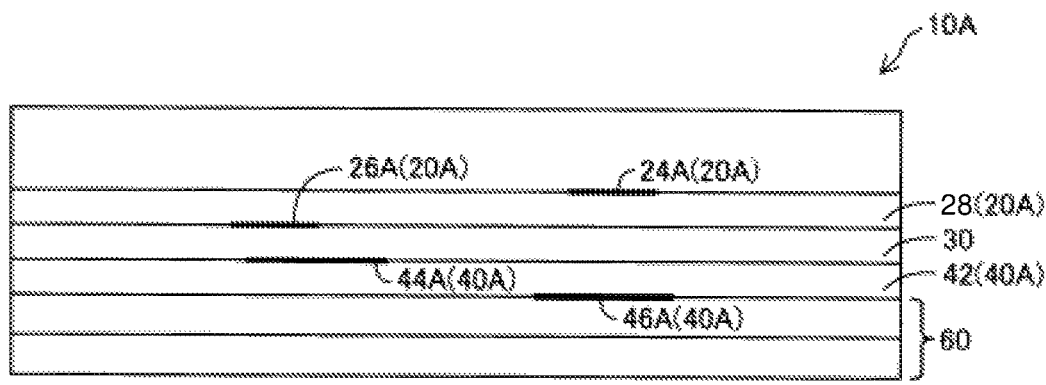
FIG. 8 is a cross-sectional view of a gas sensor element 10A in which the widthwise distance between a first lead portion 24A and a second lead portion 26A is increased.

FIG. 6 is an exploded perspective view of the gas sensor element 120A. In FIG. 6, components of the gas sensor element 120A shown are disassembled in the stacking direction (the vertical direction in the drawing sheet). The left side in the drawing sheet corresponds to the forward end side of the gas sensor element 120A, and the right side corresponds to the rear end side. In FIG. 6, dot-dash lines indicate that components connected by the dot-dash lines electrically communicate with each other.

The oxygen pump cell 135 includes a plate-shaped first solid electrolyte body 136A and electrodes (the first electrode 137 and the second electrode 138) disposed on opposite principal surfaces, respectively, of the first solid electrolyte body 136A. More specifically, the first electrode portion 137M and first lead portion 137L of the first electrode 137 and the second electrode portion 138M and second lead portion 138L of the second electrode 138 are disposed on the first solid electrolyte body 136A. The first solid electrolyte body 136A is a plate-shaped member formed mainly of zirconia ($ZrO_2$). The fourth and fifth through-hole conductors 14 and 15 that electrically communicate with the second and third through-hole conductors 12 and 13, respectively, formed in the protection layer 131 are formed in a rear end portion of the first solid electrolyte body 136A so as to extend through the first solid electrolyte body 136A.

The oxygen concentration detection cell 150 includes a plate-shaped second solid electrolyte body 151A and electrodes (the third electrode 152 and the fourth electrode 153) disposed on opposite principal surfaces, respectively, of the second solid electrolyte body 151A. More specifically, the third electrode portion 152M and third lead portion 152L of the third electrode 152 and the fourth electrode portion 153M and fourth lead portion 153L of the fourth electrode 153 are disposed on the second solid electrolyte body 151A. The second solid electrolyte body 151A is a plate-shaped member formed mainly of zirconia ($ZrO_2$). The eighth through-hole conductor 18 is formed in a rear end portion of the second solid electrolyte body 151A so as to extend through the second solid electrolyte body 151A. The eighth through-hole conductor 18 electrically communicates with the sixth through-hole conductor 16 formed in the insulating layer 145.

Also in this gas sensor element 120A, when its cross section is bisected into two regions with respect to the width direction, the first lead portion 137L is disposed in a region different from the region in which the second lead portion 138L is disposed, and the third lead portion 152L is disposed in a region different from the region in which the fourth lead portion 153L is disposed. Therefore, their widthwise separation distances can be increased, and the cells can perform accurate sensing and detection. In the gas sensor element 120A, the second lead portion 138L and the third lead portion 152L are disposed in the same region. Therefore, when a single common electrode pad, i.e., the third electrode pad 127, is used for the second lead portion 138L and the third lead portion 152L, the through-hole conductors (the third through-hole conductor 13, the fifth through-hole conductor 15, and the seventh through-hole conductor 17) connected to the third electrode pad 127 and through holes for these through-hole conductors can be easily formed. In addition, in the gas sensor element 120A, in the cross section, the second lead portion 138L and the third lead portion 152L are disposed so as to be spaced apart from each other in the width direction with no overlap as viewed in the stacking direction. Therefore, the generation of gaps in the gas sensor element 120A can be suppressed, and a reduction in the strength of the gas sensor element 120A can be suppressed.

DESCRIPTION OF REFERENCE NUMERALS

11: first through-hole conductor
12: second through-hole conductor
13: third through-hole conductor
14: fourth through-hole conductor
15: fifth through-hole conductor
16: sixth through-hole conductor
17: seventh through-hole conductor
18: eighth through-hole conductor
100: gas sensor 101: protector
101c: introduction hole
103: outer tube
110: metallic shell
110b: tool engagement portion
110c: through hole
110k: end portion
111: step portion
113: ceramic holder
113c: through hole
114: first powder layer
115: second powder layer
116: metal cup
116c: through hole
117: crimp ring
120: gas sensor element
120a: first surface
121: gas detecting section
125: first electrode pad
126: second electrode pad
127: third electrode pad
128: electrode pad
130: detecting element
131: protection layer
131a: outer surface
132: porous section
135: oxygen pump cell
136: solid electrolyte body
136a: first surface
136b: second surface
137: first electrode
137L: first lead portion
137M: first electrode portion
138: second electrode
138L: second lead portion
138M: second electrode portion
139: first insulating layer
145: insulating layer
145c: measurement chamber
146: diffusion controlling portion
150: oxygen concentration detection cell
151: solid electrolyte body
151a: first surface
151b: second surface
152: third electrode
152L: third lead portion
152M: third electrode portion
153: fourth electrode
153L: fourth lead portion
153M: fourth electrode portion
154: second insulating layer
160: heater
161: first insulator
162: second insulator
162b: outer surface
163: heat-generating resistor
164: heater lead portion
170: ceramic sleeve
170c: axial hole
181: separator
181c: through hole
182: connection terminal
185: connection terminal
190: urging metal member
191: grommet
193: sensor lead wire
196: heater lead wire AX: imaginary center axis
PS: dash-dot-dot line
S: dot-dash line
X: distance

The invention claimed is:

1. A gas sensor element comprising:
a plate shape extending in a lengthwise direction;
a first cell including a first solid electrolyte body and further including a first electrode portion and a second electrode portion that are disposed on opposite principal surfaces, respectively, of the first solid electrolyte body;
a second cell including a second solid electrolyte body and further including a third electrode portion and a fourth electrode portion that are disposed on opposite principal surfaces, respectively, of the second solid electrolyte body;
a measurement chamber disposed between the first cell and the second cell, the second electrode portion of the first cell and the third electrode portion of the second cell being exposed to the measurement chamber;
a first lead portion electrically connected to the first electrode portion and extending from the first electrode portion in the lengthwise direction;
a second lead portion electrically connected to the second electrode portion and extending from the second electrode portion in the lengthwise direction;
a third lead portion electrically connected to the third electrode portion and extending from the third electrode portion in the lengthwise direction; and
a fourth lead portion electrically connected to the fourth electrode portion and extending from the fourth electrode portion in the lengthwise direction;
wherein, in a cross section of the gas sensor element which is perpendicular to the lengthwise direction and through which the first to fourth lead portions penetrate,
when the cross section is bisected into two regions with respect to a width direction of the gas sensor element, the first lead portion and the fourth lead portion are disposed in one of the regions and the second lead portion and the third lead portion are disposed in the other region, and
the second lead portion and the third lead portion are disposed so as to be spaced apart from each other in the width direction with no overlap as viewed in a stacking direction of the gas sensor element.

2. The gas sensor element according to claim 1, wherein the first to fourth lead portions are disposed so as to be separated by at least 0.4 mm from side surfaces of the gas sensor element located on opposite sides thereof with respect to the width direction.

3. The gas sensor element according to claim 1, wherein a distance between the second lead portion and the third lead portion in the stacking direction is shorter than a distance between the first lead portion and the fourth lead portion in the stacking direction.

4. The gas sensor element according to claim 1, further comprising:
a first insulating layer that has a plate shape, surrounds a circumference of the first solid electrolyte body, and forms part of side surfaces of the gas sensor element located on opposite sides thereof with respect to the width direction, the first lead portion and the second lead portion being disposed on opposite principal surfaces, respectively, of the first insulating layer; and a second insulating layer that has a plate shape, surrounds a circumference of the second solid electrolyte body, and forms part of the side surfaces of the gas sensor element located on the opposite sides thereof with respect to the width direction, the third lead portion and the fourth lead portion being disposed on opposite principal surfaces, respectively, of the second insulating layer.

5. The gas sensor element according to claim 1, wherein the first solid electrolyte body forms part of side surfaces of the gas sensor element located on opposite sides thereof with respect to the width direction, the first lead portion and the second lead portion being disposed on opposite principal surfaces, respectively, of the first solid electrolyte body, and the second solid electrolyte body forms part of the side surfaces of the gas sensor element located on the opposite sides thereof with respect to the width direction, the third lead portion and the fourth lead portion being disposed on opposite principal surfaces, respectively, of the second solid electrolyte body.

6. A gas sensor comprising:

the gas sensor element according to claim 1;

a metallic shell having a tubular shape and surrounding a circumference of the gas sensor element; and a packed powder disposed between the gas sensor element and the metallic shell to fix the gas sensor element to the metallic shell.

7. The gas sensor according to claim 6, wherein, in a cross section of a portion of the gas sensor element which contacts the packed powder and is perpendicular to the lengthwise direction, when the cross section is bisected into two regions with respect to the width direction of the gas sensor element, the first lead portion and the fourth lead portion are disposed in one of the regions, and the second lead portion and the third lead portion are disposed in the other region, and the second lead portion and the third lead portion are disposed so as to be spaced apart from each other in the width direction with no overlap as viewed in the stacking direction.

8. The gas sensor element according to claim 1, wherein the first to fourth lead portions are disposed at different vertical positions from each other in the stacking direction.

9. The gas sensor element according to claim 1, wherein the first solid electrolyte body is substantially larger than either the first electrode portion or the second electrode portion.

10. The gas sensor element according to claim 1, wherein the second solid electrolyte body is substantially larger than either the third electrode portion or the fourth electrode portion.

11. The gas sensor element according to claim 1, further comprising:

a protective layer disposed above the first cell in the stacking direction, said protective layer including electrode pads therein.

* * * * *